United States Patent
Duncan

(10) Patent No.: US 11,491,277 B2
(45) Date of Patent: Nov. 8, 2022

(54) SYRINGE WITH MULTI-STAGE FILLING AND DISPENSING

(71) Applicant: MonuMedical, LLC, Roseville, CA (US)

(72) Inventor: David R. Duncan, Penryn, CA (US)

(73) Assignee: MonuMedical, LLC, Roseville, CA (US)

( * ) Notice: Subject to any disclaimer, the term of this patent is extended or adjusted under 35 U.S.C. 154(b) by 309 days.

(21) Appl. No.: 16/538,036

(22) Filed: Aug. 12, 2019

(65) Prior Publication Data
US 2020/0046900 A1 Feb. 13, 2020

Related U.S. Application Data

(60) Provisional application No. 62/718,156, filed on Aug. 13, 2018.

(51) Int. Cl.
| | | |
|---|---|---|
| *A61M 5/19* | (2006.01) | |
| *A61M 5/315* | (2006.01) | |
| *A61M 5/32* | (2006.01) | |
| *A61M 5/178* | (2006.01) | |

(52) U.S. Cl.
CPC .......... *A61M 5/19* (2013.01); *A61M 5/31596* (2013.01); *A61M 5/3294* (2013.01); *A61M 2005/1787* (2013.01)

(58) Field of Classification Search
CPC ...... A61M 2005/1787; A61M 5/31596; A61M 5/3294; A61M 5/19; A61M 5/1408; A61M 5/16827; A61M 5/1782; A61M 5/3129; A61M 2005/3132
See application file for complete search history.

(56) References Cited

U.S. PATENT DOCUMENTS

| | | |
|---|---|---|
| 212,046 A | 2/1879 | Palmer |
| 453,322 A | 6/1891 | Beekman |
| 553,234 A | 1/1896 | Finot |
| 708,224 A | 9/1902 | Gundlach |
| 857,739 A * | 6/1907 | Kennerly .............. A61M 5/204 604/183 |
| 1,014,608 A | 1/1912 | Pernice |
| 1,930,929 A | 10/1933 | Eisenberg |
| 3,976,068 A | 8/1976 | Lundquist |

(Continued)

FOREIGN PATENT DOCUMENTS

WO  WO 2013/112579  8/2013

*Primary Examiner* — Theodore J Stigell
(74) *Attorney, Agent, or Firm* — Heisler & Associates

(57) ABSTRACT

The syringe includes a hollow body with at least one free-floating piston and a plunger within the body, with the piston between the plunger and a proximal end of the body. A manifold is provided lateral to the body. The manifold leads to an input/output tip. The manifold includes a front port located between the piston and the proximal end of the body and a rear port spaced from the proximal end of the body. The manifold includes at least one flow path leading from the input/output tip to at least one of the front port and/or the rear port. A first fluid fills a rear chamber distal to the piston and then the manifold is adjusted to fill second fluid into a front chamber proximal of the piston, and then the manifold is adjusted to allow sequential delivery of the second fluid and the first fluid.

5 Claims, 5 Drawing Sheets

(56) References Cited

U.S. PATENT DOCUMENTS

| | | | |
|---|---|---|---|
| 4,610,666 A * | 9/1986 | Pizzino | A61M 5/19 604/191 |
| 4,643,721 A | 2/1987 | Brunet | |
| 4,668,223 A | 5/1987 | Grotenhuis | |
| 4,758,235 A | 7/1988 | Tu | |
| 4,792,329 A | 12/1988 | Schreuder | |
| 4,929,230 A | 5/1990 | Pfleger | |
| 5,171,220 A | 12/1992 | Morimoto | |
| 5,236,420 A | 8/1993 | Pfleger | |
| 5,298,024 A | 3/1994 | Richmond | |
| 5,695,465 A | 12/1997 | Zhu | |
| 5,704,918 A | 1/1998 | Higashikawa | |
| 5,713,857 A | 2/1998 | Grimard | |
| 5,720,732 A | 2/1998 | Whisson | |
| 5,743,886 A | 4/1998 | Lynn | |
| 5,743,890 A | 4/1998 | Hjertman | |
| 5,785,682 A | 7/1998 | Grabenkort | |
| 5,830,193 A | 11/1998 | Higashikawa | |
| 5,851,200 A | 12/1998 | Higashikawa | |
| 5,899,881 A | 5/1999 | Grimard | |
| 6,027,481 A | 2/2000 | Barrelle | |
| 6,077,252 A | 6/2000 | Siegel | |
| 6,120,478 A | 9/2000 | Moore | |
| 6,132,400 A | 10/2000 | Waldenburg | |
| 6,142,977 A | 11/2000 | Kolberg | |
| 6,149,628 A | 11/2000 | Szapiro | |
| 6,161,364 A | 12/2000 | Kolberg | |
| 6,544,233 B1 | 4/2003 | Fukui | |
| 6,602,223 B2 | 8/2003 | Szapiro | |
| 6,622,721 B2 | 9/2003 | Vedrine | |
| 6,641,561 B1 | 11/2003 | Hill | |
| 6,723,074 B1 | 4/2004 | Halseth | |
| 6,740,062 B2 | 5/2004 | Hjertman | |
| 6,866,653 B2 | 3/2005 | Bae | |
| 7,319,725 B2 | 1/2008 | Kopmeiners | |
| 7,789,862 B2 | 9/2010 | Thorne, Jr. | |
| 7,998,106 B2 | 8/2011 | Thorne, Jr. | |
| 8,016,789 B2 | 9/2011 | Grant | |
| 8,034,026 B2 | 10/2011 | Grant | |
| 8,066,672 B2 | 11/2011 | Mandro | |
| 8,075,533 B2 | 12/2011 | Lee | |
| 8,075,547 B2 | 12/2011 | Lee | |
| 8,113,244 B2 | 2/2012 | Kamen | |
| 8,152,778 B2 | 4/2012 | Chebator | |
| 8,162,875 B2 | 4/2012 | Braga | |
| 8,223,028 B2 | 7/2012 | Mandro | |
| 8,262,616 B2 | 9/2012 | Grant | |
| 8,267,892 B2 | 9/2012 | Spencer | |
| 8,403,180 B2 | 3/2013 | Nakatsuka | |
| 8,414,522 B2 | 4/2013 | Kamen | |
| 8,414,563 B2 | 4/2013 | Kamen | |
| 8,430,843 B2 | 4/2013 | Chebator | |
| 8,454,564 B2 | 6/2013 | Deppisch | |
| 8,491,570 B2 | 7/2013 | Kamen | |
| 8,496,646 B2 | 7/2013 | Kamen | |
| 8,529,517 B2 | 9/2013 | Lee | |
| 8,544,682 B2 | 10/2013 | Fransson | |
| 8,545,445 B2 | 10/2013 | Kamen | |
| 8,585,377 B2 | 11/2013 | Kamen | |
| 8,665,998 B2 | 3/2014 | Kopmeiners | |
| 8,708,376 B2 | 4/2014 | Tracey | |
| 8,936,577 B2 | 1/2015 | Lee | |
| 8,992,505 B2 | 3/2015 | Thorne, Jr. | |
| 9,173,996 B2 | 11/2015 | Gray | |
| 9,180,245 B2 | 11/2015 | Bryant | |
| 9,180,249 B2 | 11/2015 | Hallahan | |
| 9,351,905 B2 | 5/2016 | Grow | |
| 9,526,830 B2 | 12/2016 | Kamen | |
| 9,950,114 B2 * | 4/2018 | Thorne, Jr. | A61M 5/365 |
| 2002/0094041 A1 | 7/2002 | Kopmeiners | |
| 2006/0142701 A1 | 6/2006 | Thorne, Jr. | |
| 2006/0224105 A1 | 10/2006 | Thorne, Jr. | |
| 2006/0258977 A1 | 11/2006 | Lee | |
| 2007/0049870 A1 | 3/2007 | Gray | |
| 2007/0219480 A1 | 9/2007 | Kamen | |
| 2007/0219496 A1 | 9/2007 | Kamen | |
| 2007/0219597 A1 | 9/2007 | Kamen | |
| 2007/0228071 A1 | 10/2007 | Kamen | |
| 2008/0319400 A1 | 12/2008 | Thorne, Jr. | |
| 2009/0062740 A1 | 3/2009 | Thorne, Jr. | |
| 2009/0088724 A1 | 4/2009 | Chebator | |
| 2009/0281497 A1 | 11/2009 | Kamen | |
| 2009/0287184 A1 | 11/2009 | Lee | |
| 2009/0299289 A1 | 12/2009 | Kamen | |
| 2010/0082013 A1 | 4/2010 | Braga | |
| 2010/0082015 A1 | 4/2010 | Chebator | |
| 2010/0089475 A1 | 4/2010 | Tracey | |
| 2010/0094215 A1 | 4/2010 | Grant | |
| 2010/0094222 A1 | 4/2010 | Grant | |
| 2010/0114068 A2 | 5/2010 | Lee | |
| 2010/0292672 A1 | 11/2010 | Lee | |
| 2010/0327007 A1 | 12/2010 | Fransson | |
| 2011/0017777 A1 | 1/2011 | Nakatsuka | |
| 2011/0160664 A1 | 6/2011 | Deppisch | |
| 2012/0323173 A1 | 12/2012 | Thorne, Jr. | |
| 2013/0116657 A1 | 5/2013 | Hallahan | |
| 2014/0060664 A1 | 3/2014 | Abbott | |
| 2014/0276039 A1 * | 9/2014 | Cowan | A61M 5/31513 600/432 |
| 2014/0346071 A1 | 11/2014 | Genosar | |

\* cited by examiner

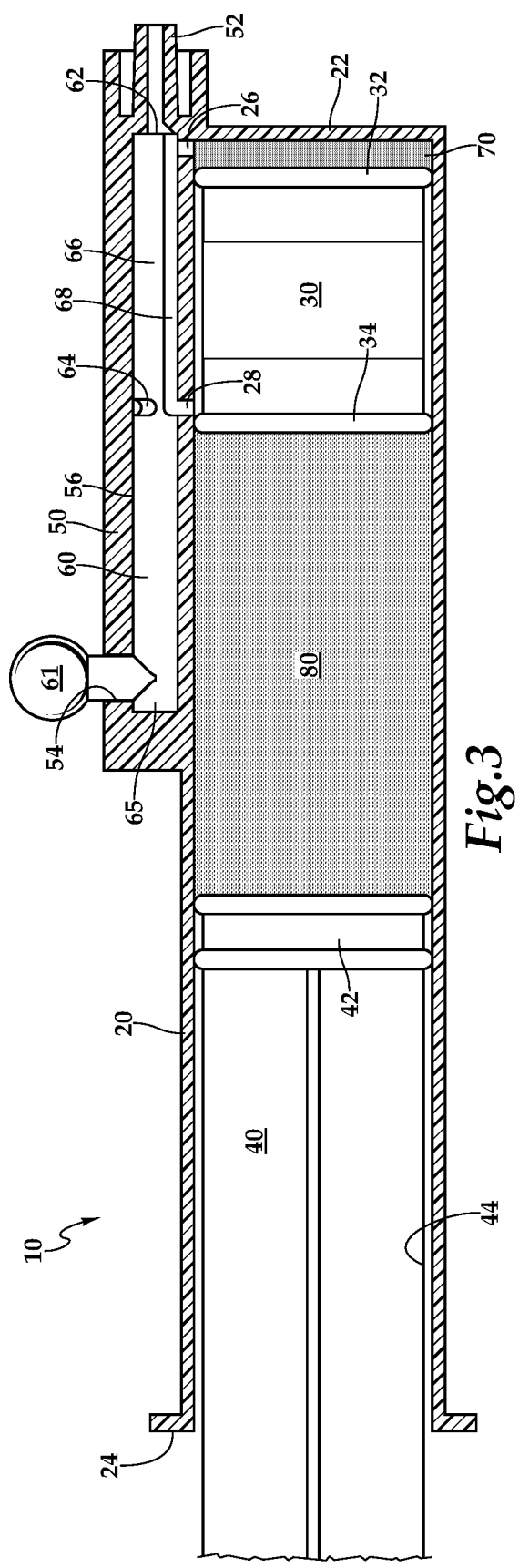

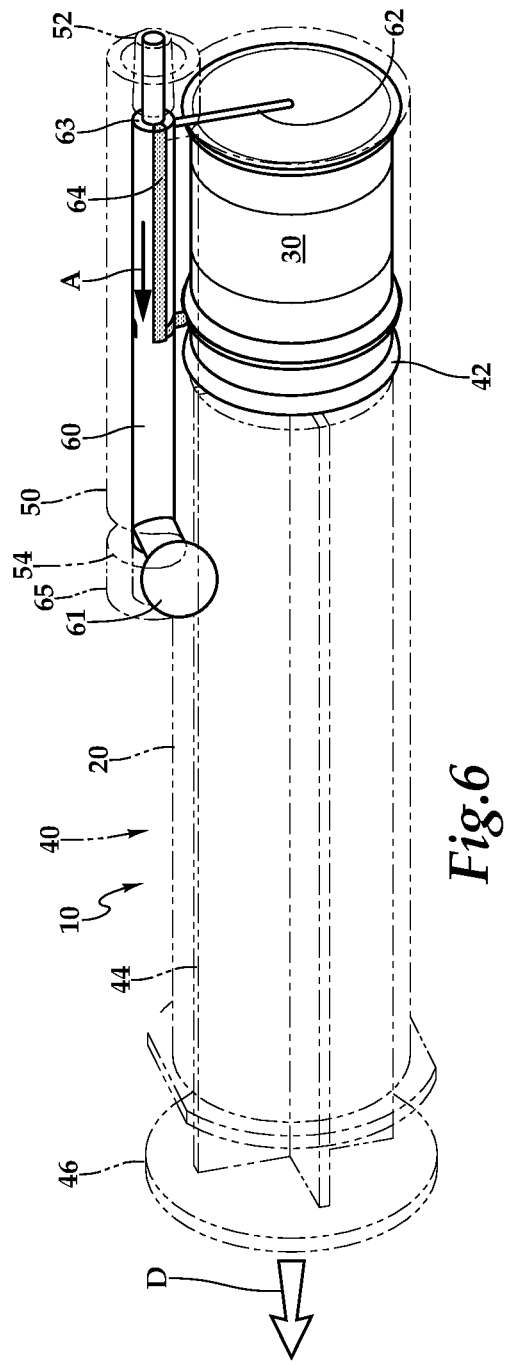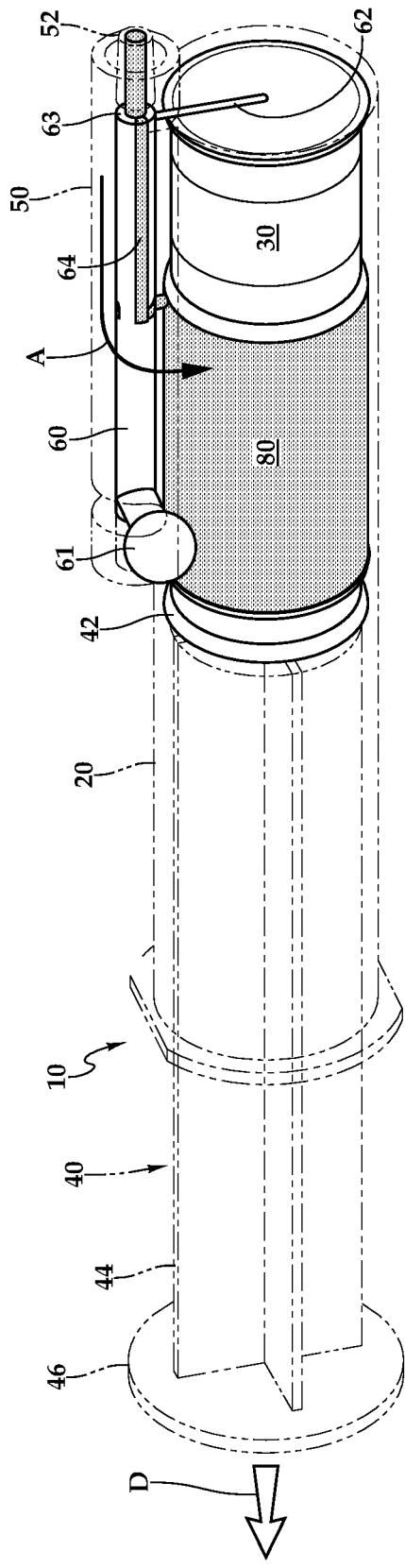

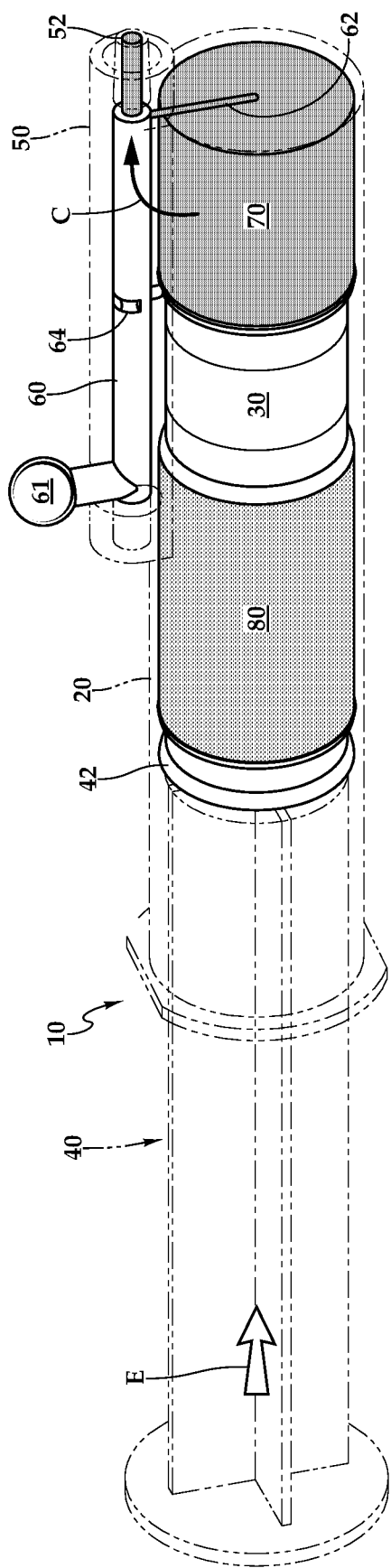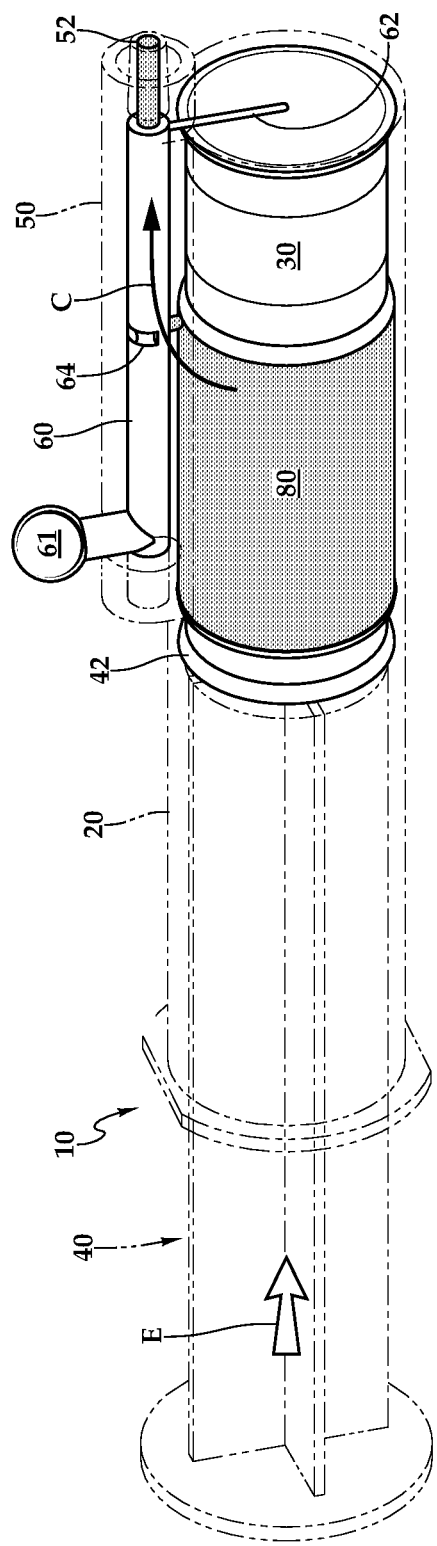

SYRINGE WITH MULTI-STAGE FILLING AND DISPENSING

CROSS-REFERENCE TO RELATED APPLICATIONS

This application claims benefit under Title 35, United States Code § 119(e) of U.S. Provisional Application No. 62/718,156 filed on Aug. 13, 2018.

FIELD OF THE INVENTION

The following invention relates to syringes for delivering multiple separate fluids. More particularly, this invention relates to syringes which have two or more chambers within a common body which can be separately filled and separately dispensed, such as for the sequential delivery of medicaments.

BACKGROUND OF THE INVENTION

Syringes are known in the prior art for delivering medicament to a patient, and for other purposes. One basic form of syringe includes a hollow cylindrical body with the first end proximal to the patient or other delivery location and called the proximal end and a second end proximal to the user of the syringe and called the distal end. A plunger resides within the body with a seal on a proximal end of the plunger. A tip acts as an inlet/outlet for the syringe and communicates with an inner chamber of the body through the proximal end. When the plunger is retracted distally, and toward a user, a vacuum is drawn between the seal on the proximal end of the plunger and the proximal end of the body, which causes a fluid to be sucked in through the tip of the syringe. This process is reversed by pushing the plunger proximally and away from the user to dispense medicament from the syringe and through the outlet.

In many circumstances multiple liquids (or other fluids) need to be delivered. In the medical arts, one example includes when a first medicament is delivered, followed by delivery of a "saline flush" after the medicament. Such a saline flush is often needed because the delivery of medicament is into some medical tubing circuitry which still contains some of the medicament after it is delivered by the syringe. To avoid leaving the medicament within the circuitry, at least partially, and to get all of the medicament into the patient, the saline flush can be utilized to push all of the medicament into the patient and clear the medical tubing circuitry of any remaining medicament.

In some circumstances medicament delivery needs to happen with some degree of rapidity and then also needs to be rapidly followed by a saline flush or delivery of a second medicament or other liquid to neutralize or otherwise altar the initial medicament that was delivered or provide a complementary therapeutic effect. Often administration of adenosine follows such a protocol. Whenever two medicaments or other liquids need to be delivered, the standard single syringe described above is only able to perform half of the necessary task.

One option for delivering two medicaments or other liquids utilizing standard syringes includes loading one syringe with both medicaments. This does not allow sequential delivery, and with saline flush, leaves medicament within the infusion lines. Also, volume of delivery errors are exacerbated, since the user needs to do some calculations to load the syringe to a proper volume. Another option in the prior art includes first delivering the medicament with a first syringe through some access point, then disconnecting the first syringe, connecting a second syringe at that access point, and then delivering the second medicament or other liquid with the second syringe. This option is time consuming and requires two syringes.

Another option includes attaching two separate syringes loaded with the two separate medicaments or other liquids and then connecting these two syringes separately into an access point, such as through a stopcock which can receive multiple inputs feeding to at least one output which accesses the patient or other source for the liquids. The stopcock is manipulated to cause the first syringe to be in communication with the patient, and then the first syringe is utilized to deliver the first medicament or other liquid. Then the stopcock is manipulated to cause the second syringe to be in communication with the patient. Finally, the second syringe is utilized to deliver the second medicament or other liquid through the stopcock to the patient. As one can see, this is a rather elaborate procedure, involves difficulty in achieving rapid infusion, as well as presents multiple opportunities for mistakes.

Accordingly, a need exists for a syringe which can deliver two medicaments from a single syringe in a simple, rapid and reliable fashion. Furthermore, other industries and circumstances call for simple, rapid and reliable delivery of fluids. Such industries/situations include laboratory science, manufacturing with two part adhesives or other two (or more) part reactions (especially with a time sensitive/critical element to the reactions), and related circumstances.

SUMMARY OF THE INVENTION

With this invention, a single syringe is provided which has two or more separate in-line chambers and a single tip which provides an input/output for the syringe. The syringe has a familiar generally standard configuration in a preferred embodiment. This standard configuration includes a cylindrical body with a hollow core and a plunger extending out of a distal end of the body, and with a tip for input/output of medicaments or other fluids at a proximal end thereof (or at least adjacent thereto).

Uniquely with this invention, a free floating piston is provided between a seal at a proximal end of the plunger and the proximal end of the body of the syringe. Thus, when this piston moves distally and the plunger moves distally, two separate chambers can be created within the body. This piston has at least one seal thereon or can seal along its length at a lateral surface thereof, or may have two seals, one on each end of the free floating piston.

The multi-stage syringe also has an adjustable manifold with a control knob or other user interface associated therewith. This control knob has a first position which causes the tip to have a fluid access flow path distal of the piston and proximal of the plunger seal, for filling of a rear chamber on a distal side of the piston. The control knob has a second position which causes the tip of the syringe to be in fluid communication with a proximal end of the piston and adjacent to the proximal end of the body of the syringe, for filling of a front chamber between the piston and the proximal end of the body of the syringe.

Finally, the control knob has a third position where both the front chamber adjacent to the proximal end of the body of the syringe and the rear chamber between the proximal plunger seal and the rear seal of the piston, can both have access to the tip, preferably in stages, with first access to this tip provided for the front chamber, followed by access for the rear chamber (typically after the piston has moved approximately up against the proximal end of the syringe). Thus, when the control knob is in this third delivery position, pushing of the plunger causes fluid in the front chamber to first pass through the manifold to the tip and then for fluid in the rear chamber to then be aligned with the manifold and tip for delivery of medicament or other liquid from the rear chamber, through further pushing of the plunger of the syringe.

A particular embodiment of the invention is disclosed in the included figures, and show sequential steps in loading of the two chambers in the two stage version of the multi-stage syringe, followed by dispensing. In this disclosed embodiment, both loading of the syringe and dispensing from the syringe occur in a familiar standard syringe fashion by retracting the plunger first, followed by pushing of the plunger. The only difference is that the control knob of the manifold is positioned where required for filling of the first chamber, usually the rear chamber, followed by control knob repositioning and filling of the second chamber (usually the front chamber), and then control knob repositioning to open both chambers and allowing the medicament to be delivered in sequential fashion from the front (proximal) chamber and the rear (distal) chamber.

Most preferably, the body is at least partially transparent so that an operator can see the two chambers filling. Furthermore, graduation lines can be provided on opposite sides of the syringe. A first set of graduation lines include a legend such as "rear volume" and has numbers (or other indicia) indicating how much volume has been provided into the rear chamber (which would typically be the first chamber to be filled). These graduation lines start with a zero line which lines up with a distal end of the piston. On the opposite side of the body, separate graduation lines are provided with a legend such as "front volume" and with volume indicia adjacent corresponding graduation lines. These graduation lines associated with the front volume start with a "zero" graduation line adjacent to the proximal end of the body.

Furthermore, most preferably the rear volume is filled into the rear chamber when the control knob is moved toward the side of the syringe body which has the rear volume graduation lines thereon. When the control knob is rotated toward the front volume graduation lines, its associated manifold lines are configured for filling of the front chamber. A knob position that is between these two positions can be utilized for staged, sequential delivery of medicaments or other fluids, first from the front chamber and then from the rear chamber.

In one embodiment, the manifold pathways are contained within a cylinder mounted lateral to the main body of the syringe. This lateral cylinder can support the tip of the syringe with associated structure, such as male Luer lock fitting structures, for attachment to a patient, through various intravenous access lines as is known in the art. This lateral cylinder (also called a manifold chamber) has a manifold valve control shaft therein which substantially fills this lateral cylinder.

The manifold shaft has paths formed on an outer surface thereof (or optionally passing through interior pathways within the shaft). These paths all lead to a proximal end of the manifold shaft and feed the inlet/outlet tip where the Luer end resides. These paths also extend distally along the manifold shaft varying distances to access the different chambers (front, rear or both).

The control knob is attached to this manifold shaft so that the control knob can be utilized for translating or rotating the manifold shaft into different positions. In one embodiment, when the control knob is in a twelve o'clock position, a staged delivery path on the manifold shaft (which can access both the first chamber and the second chamber) is located adjacent to the body of the syringe. A front port adjacent to the proximal end of the body and a rear port (spaced from the proximal end of the body by a distance similar to a length of the piston) each pass through a lateral wall of the syringe body and enter into the lateral cylinder, so that fluid can pass from within the body of the main cylinder through to within the interior of the lateral cylinder, provided that the manifold shaft is rotated into a position which "opens" the front port and/or the rear port.

When the control knob is in the twelve o'clock position and the staged delivery path in the manifold shaft is aligned with both the front port and the rear port, pushing of the plunger causes delivery of medicament from the front chamber through the staged delivery path, which is formed within the manifold shaft, and then accesses a proximal end of the lateral cylinder which supports the tip, for delivery of the medicament or other liquid from this tip which would typically be a male Luer end. Once the piston has moved approximately adjacent to the proximal end of the body of the syringe, the rear port is then "opened" and has access to this staged delivery path, so that continued pushing of the plunger causes medicament or other liquid within the rear chamber to be delivered along the staged delivery path of the control manifold into and through the lateral cylinder and out to the tip for delivery to the patient.

When the control knob is in a three o'clock position in this embodiment, the rear path is aligned with the rear port so that retraction of the plunger causes medicament or other liquid to be drawn through the tip, along the rear path in the manifold shaft, and then through the rear port and into the rear chamber on a distal side of the piston and a proximal side of the plunger seal.

Once this rear chamber is filled a desired amount (following the adjacent graduation lines and indicia for the rear chamber), the control knob is rotated to the nine o'clock position, which causes a front path in the manifold shaft to be aligned with the front port. Now, as the plunger is pulled back, it also pulls back the fluid in the rear chamber and the piston, as a unit, during which medicament or other liquid is drawn through the tip, along the front path in the manifold shaft, and into the front chamber. The multi-stage syringe is thus loaded with two separate medicaments or other liquids. Rotating of the control knob to the dispensing orientation (twelve o'clock in this embodiment) configures the syringe that the plunger can be merely pushed in a continuous motion to first deliver medicament or other liquid from the front chamber, followed by delivery of medicament or other liquid from the rear chamber.

Other configurations for the syringe could alternatively be provided. The manifold structure disclosed in this embodiment in the form of the lateral cylinder to the main body, could instead be in-line with the main body or contained within the main body, and adjacent to the proximal end, for instance. While the control knob is manual in form, it could alternatively be in the form of an electric, pneumatic, or other control with buttons or other user input/control. With the simple form shown in the disclosed embodiment, the plunger can be fully removed and with appropriate pressure applied into the front chamber, the piston can also be pushed out of the rear of the body. The plunger and piston can thus be fully cleaned, sterilized, etc. and then re-inserted should be syringe be desired to be reused. Similarly, the manifold shaft can be configured to be removable from the lateral cylinder, such as for cleaning and sterilizing and potential reuse. As an alternative, the syringe could be designed for single use, followed by recycling or other disposal.

In one embodiment, the rear chamber is preloaded, such as with a saline flush. This syringe could be provided within a kit and preloaded with the saline (or other liquid). A user would then take the multi-stage syringe out of the kit, connect it to a source of medicament, configure the manifold shaft for filling (or adjust some other control for filling), and then retract the plunger to fill the syringe with the desired amount of medicament or other liquid into the front chamber. The control could be fixed in one position as an alternative, which loads/aspirates the front chamber only. Further plunger pushing could break a small seal and allow the saline (or other second liquid) to then follow the same path out of the syringe, so that a control-less simple partially pre-loaded syringe would be provided. If the control is provided as in previous embodiments, the control would be manipulated, such as by rotation of the control knob to a dispensing orientation, followed by plunger pushing for staged delivery of the medicament or other liquid from the front chamber, followed by the pre-loaded amount of saline flush (or other pre-filled secondary liquid) out of the syringe.

OBJECTS OF THE INVENTION

Accordingly, a primary object of the present invention is to provide a syringe which can deliver two or more separate fluids.

Another object of the present invention is to provide a single syringe with a single plunger and a single hollow cylindrical body, but which can be filled with two or more different fluids kept separate from each other and then discharge the fluids.

Another object of the present invention is to provide a syringe which can be accurately loaded with a desired amount of two or more different fluids within a single syringe.

Another object of the present invention is to provide a syringe which can be loaded with two or more different fluids and then have the fluids sequentially dispensed.

Another object of the present invention it to provide a syringe which can store two or more separate fluids without the fluids contacting each other until delivery.

Another object of the present invention is to provide a syringe with two or more separate chambers for holding two or more separate fluids, which chambers are filled and discharged by translating a single plunger.

Another object of the present invention is to simplify the process of treating a patient by delivery of multiple fluids sequentially from a single syringe.

Another object of the present invention is to provide a method for delivering two fluids sequentially to a patient, such as into a bloodstream of the patient or into other body lumens or other subcutaneous spaces of the patient.

Another object of the present invention is to provide a partially pre-loaded syringe that only needs to be loaded with one fluid to then be used to deliver two fluids.

Other further objects of the present invention will become apparent from a careful reading of the included drawing figures, the claims and detailed description of the invention.

BRIEF DESCRIPTION OF THE DRAWINGS

FIG. 3 is a side elevation view of the syringe of FIG. 1, but with the manifold in a third orientation for delivery of fluids sequentially from the front chamber and then the rear chamber, through the manifold.

FIG. 4 is a side elevation schematic of a syringe similar to that which is shown in FIGS. 1-3, except that valves are provided within the manifold, one valve for the front chamber and one valve for the rear chamber, the valves allowing selective access to the various chambers, either individually or simultaneously, depending on valve state.

FIG. 5 is a side elevation view of a portion of that which is shown in FIGS. 1-5, and further showing graduation lines and indicia in two separate arrays for measuring an amount of fluid separately filled into front and rear chambers of the multi-stage syringe.

FIGS. 6-11 are perspective views of that which is shown in FIGS. 1-3, and with the body of the syringe and most portions of a plunger of the syringe, as well as a manifold chamber of the syringe shown in broken lines, and with other portions of the syringe as well as fluids therein all shown in solid lines in a series of steps associated with filling of each of the chambers of the syringe and simultaneous discharge of fluids from the syringe.

DESCRIPTION OF THE PREFERRED EMBODIMENT

Figure 1:
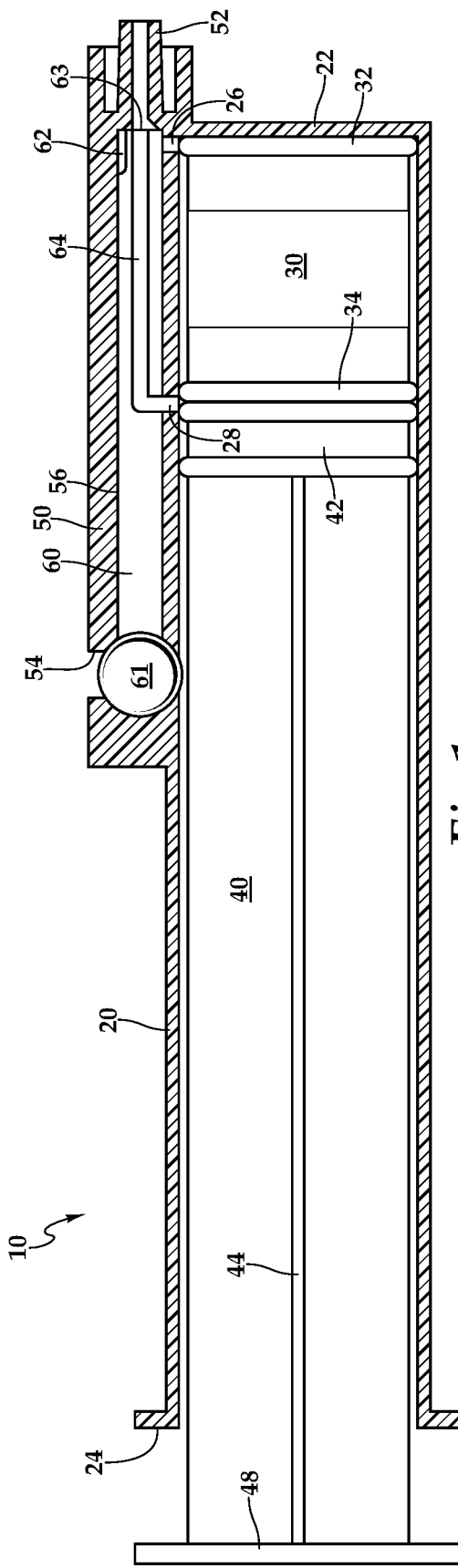
FIG. 1 is a side elevation view of a syringe according to one embodiment of this invention with an outer body and manifold of the syringe shown in full section, and with the manifold oriented in a position to provide a flow path leading to a rear chamber between a free-floating piston and a plunger of the syringe.

Referring to the drawings, wherein like reference numerals represent like parts throughout the various drawing figures, reference numeral 10 is directed to a syringe according to one embodiment of this invention, the syringe 10 being of a multi-stage variety including a front chamber 70 and a rear chamber 80, which can be selectively loaded with different fluids and then sequentially have those fluids delivered from the syringe 10. The syringe 10 is configured to be easy to use in a manner akin to that of prior art syringes, and with simple controls for reliable and safe filling and dispensing of fluids from the syringe.

Figure 2:
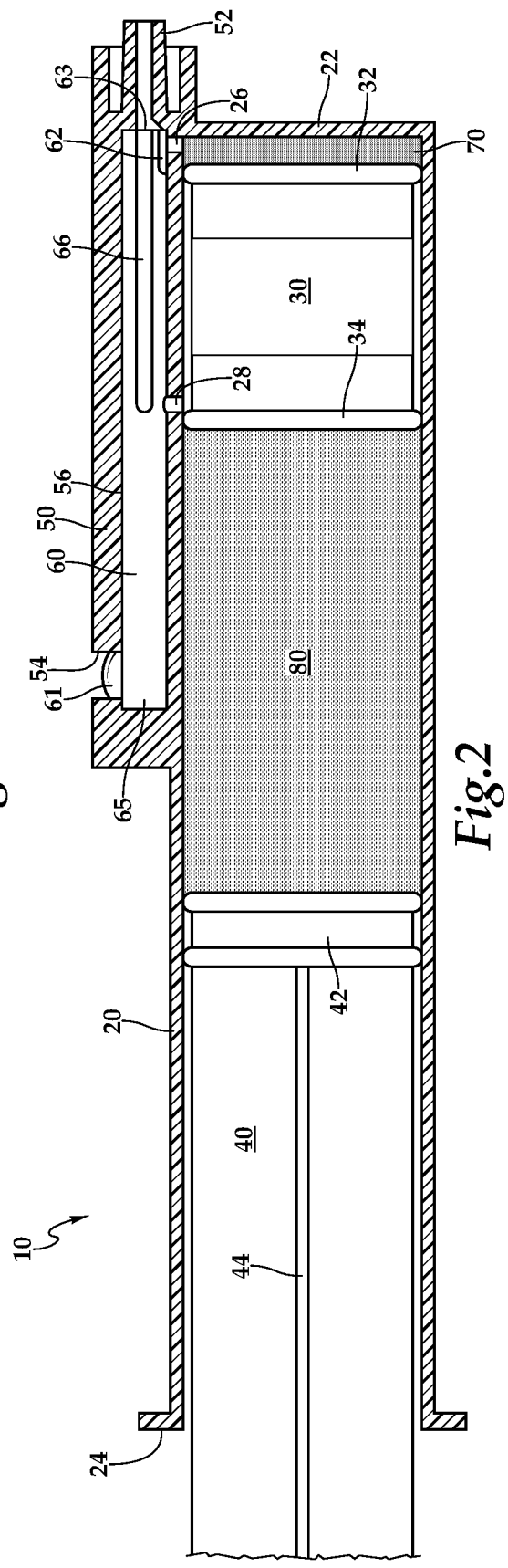
FIG. 2 is a side elevation view of the syringe of FIG. 1, but with the manifold adjusted into a second orientation for loading of fluids into a front chamber between the piston and a proximal end of the body, the syringe shown having already had a rear chamber thereof filled.
Figure 8:
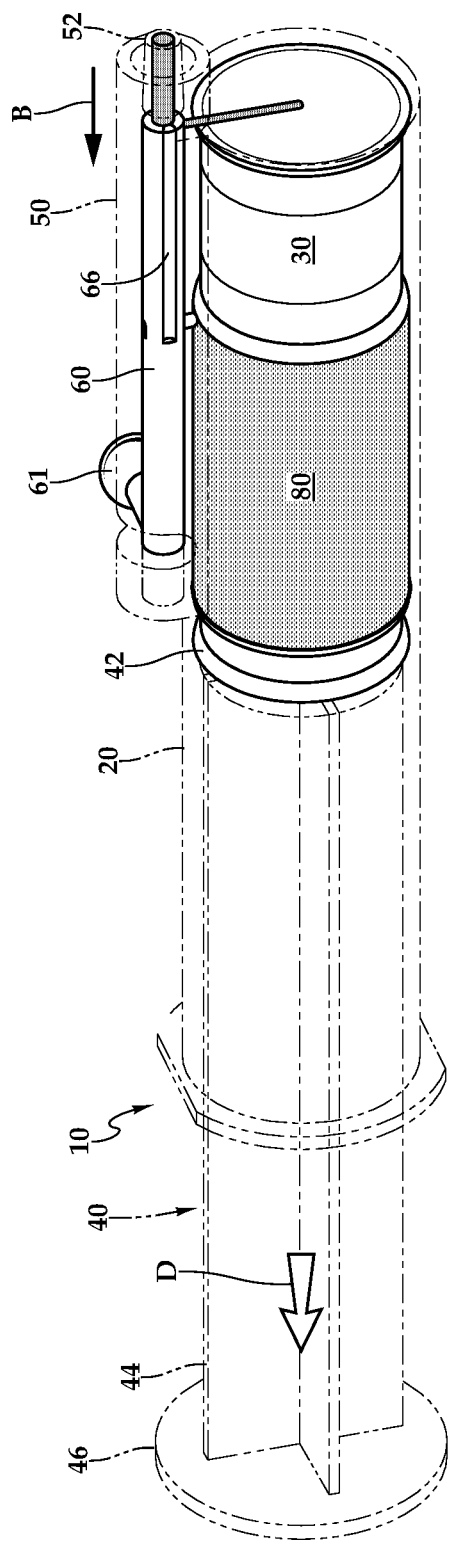
Figure 9:
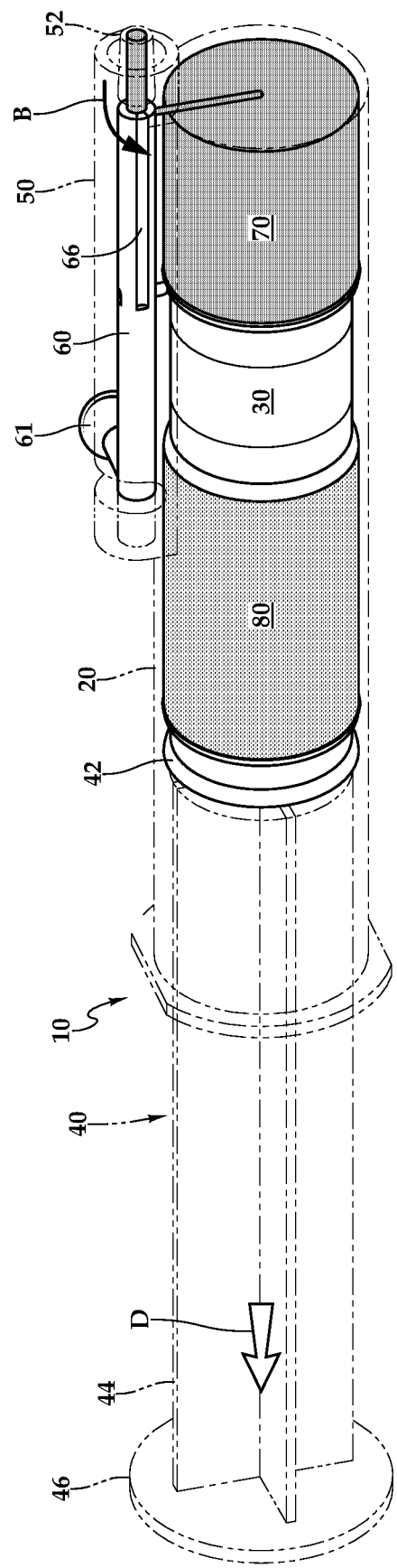

In essence, and with particular reference to FIGS. 1-3, basic details of the syringe 10 are described, according to a first embodiment. The syringe 10 includes a hollow cylindrical body 20. A free-floating piston 30 is located within the body 20 and a plunger 40 is also located within the body 20, with the free-floating piston 30 deeper into the hollow cylindrical body 20 than the plunger 40. A manifold chamber 50 is provided lateral to the body 20. This manifold chamber 50 supports an input/output tip 52 and also a front port 26 and rear port 28 leading from the manifold chamber 50 into an interior of the hollow body 20 at strategic locations on either side of the piston 30, when the piston 30 is located at a maximum depth within the hollow body 20. A manifold shaft 60 is located within the manifold chamber 50 and acts as a flow directing valve to provide a fluid path which either leads to the front port 26, the rear port 28 or a combination of both the front port 26 and rear port 28. When only one port 26, 28 is accessed, the syringe 10 is appropriately configured for loading a portion of the syringe 10 on one side of the piston 30. When both ports 26, 28 are in fluid communication with the input/output tip 52, fluids in chambers 70, 80 on either side of the piston 30 can be sequentially delivered from the front chamber 70 adjacent to the front port 26 and then the rear chamber 80 adjacent to the rear port 28.

More specifically, and with continuing reference to FIGS. 1-3, basic details of the body 20 are described, according to this example. The body 20 is an elongated hollow cylindrical structure generally having a form similar to that of many standard syringes. The body 20 preferably is at least partially transparent in form, so that the fluid and moving structures within the syringe 10 can be visualized through a wall of the body 20. The body 20 is typically formed of an at least semi-rigid plastic material, but could be formed of other materials as an alternative.

The body 20 extends from a proximal end 22 which is typically closed and most distant from a user of the syringe, to a distal end 24 which is mostly open and allows for action of a plunger 40 passing therethrough, and is closest to a user and more distal relative to a patient or other site where fluids are being collected and/or dispensed from the syringe 10. The body 20 is otherwise generally similar to a standard syringe, except that a front port 26 and rear port 28 penetrate a wall of the body 20 at strategic locations on the body 20. The front part 26 is preferably adjacent to the proximal end 22, but just to a distal side of the proximal end 22. This front port 26 thus allows fluids to pass into a space between the proximal end of the body 20 and the piston 30. Such a space expands as fluid is placed therein, and is generally referred to as a front chamber 70.

The rear port 28 is spaced from the proximal end 22 of the body 20 by a distance at least as great as a length of the piston 30. In this way, the rear port 28 accesses a space between the piston 30 and the plunger 40, which space, when filling with fluid, is defined as a rear chamber 80. These two ports 26, 28 preferably are spaced axially from each other but aligned radially relative to each other and within a common plane bisecting a centerline of the body 20 of the syringe 10. The ports 26, 28 are also provided on a side of the body 20 where the manifold chamber 50 is located, so that these ports 26, 28 generally extend and provide fluid pathways extending from an interior of the body 20 of the syringe 10 to an interior of the manifold chamber 50.

With particular continuing reference to FIGS. 1-3, details of the piston 30 and plunger 40 are described, according to this example. The piston 30 is preferably generally similar to a tip of a plunger 40 which is designed to extend into a hollow body of a syringe, except that this piston 30 does not include any shaft or hand engageable structure associated therewith. Rather, the piston 30 is merely a mass of material which is preferably substantially rigid, and which has at least one seal thereon for sealing relative to interior side walls of the hollow body 20. In the embodiment shown, the piston 30 includes a front seal 32 opposite a rear seal 34. As an alternative, the piston 30 could have a single seal running between forward and rearward ends of the piston 30, or could have only one seal at one end of the piston 30. As another alternative, more than two seals could be provided along the piston 30.

The piston 30 preferably has a friction fit within a hollow (preferably cylindrical) interior of the body 20, with this friction fit being loose enough to allow the piston 30 to relatively easily translate within the hollow interior of the body 20, in an axial direction along a centerline of the body 20, but maintain a tight seal against an interior wall of the hollow body 20. The piston 30 has a length in an axial direction generally matching spacing between the ports 26, 28 extending from an interior of the hollow body 20 into an interior of the manifold chamber 50.

With continuing reference to FIGS. 1-3, details of the plunger 40 are described, according to this exemplary embodiment. The plunger 40 is an elongate structure similar to standard syringes with a plunger seal 42 at a proximal end closest to the piston 30 and the proximal end 22 of the body 20, and a shaft 44 extends away from the plunger seal 42 to a push plate 48 which extends out of the distal end 24 of the body 20 and is configured to be easily engaged by a hand of a user (or structures of an infusion pump or other device) when the syringe 10 is to be manipulated by translation of the plunger 40 along the axial centerline of the body 20. Operation of the syringe 10 includes sliding translation of the plunger 40 within the body 20, as well as selection of a functional state of the manifold. By these two actions, which are typically provided manually by hand of the user, the syringe 10 is caused to be operated for filling with two separate fluids and then to provide sequential delivery of those fluids.

The plunger 40 is typically formed of relatively rigid plastic material, typically the same plastic from which the body 20 of the syringe 10 is formed. The plunger seal 42 has many characteristics similar to those of the piston 30, except that the plunger seal 42 typically has a lesser length axially within the body 20 as the length of the piston 30. The plunger seal 42 could have a variety of different numbers of seals on the perimeter thereof to have a friction fit but still be capable of translation movement, and maintaining a fluid tight seal at a perimeter of this plunger seal 42.

With continuing reference to FIGS. 1-3, as well as somewhat to FIGS. 6-11, details of the manifold are described, including both the manifold chamber 50 and a manifold shaft 60. The manifold provides one form of a fluid pathway (also called a flow path) which is adjustable and extending from an input/output tip 42 adjacent to the proximal end of the syringe 10 and the various chambers 70, 80 associated with the front port 26 and rear port 28 within the body 20, and on either side of the piston 30. This manifold could have a variety of different configurations, with the particular configuration of the manifold chamber 50 and manifold shaft 60 illustrating one effective embodiment for this invention, where fluid pathways are selected by rotation of the manifold shaft 60 into various different rotational positions as described in detail below.

The manifold chamber 50 is preferably a rigid hollow elongate structure. In this embodiment, the manifold chamber 50 has a centerline parallel with a central axis of the body 20, with the manifold chamber 50 laterally spaced from the body 20 and directly adjacent to an outer surface of the body 20. The manifold chamber 50 extends from the tip 52, which is preferably generally near the proximal end 22 of the body 20, but most typically extends slightly beyond into a proximal side of the proximal end 22 most distant from the plunger 40. This tip 52 could be fitted with a needle or other fluid handling element, but most typically is filled with a Luer lock coupling which allows for various different structures to be attached thereto, including medical tubing, stopcocks, needles, and other suitable fluid handling apparatuses.

The manifold chamber 50 preferably has a generally cylindrical hollow interior open to this tip 52, and extending rearwardly (distally). A portion of the manifold chamber 50 most distant from the tip 52 is preferably closed off, except that a central bore 56 thereof is open to a control slot 54 extending laterally from the centerline of the central bore 56.

The manifold shaft 60 resides within the central bore 56 of the manifold chamber 50. The manifold shaft 60 has most preferably multiple fluid pathways formed therein which can be selectively aligned with the front port 26 and/or rear port 28 to cause the manifold to be reconfigured into various different states. Most preferably, three fluid paths are provided on the manifold shaft 60, each embedded on the exterior surface of the manifold shaft 60 which otherwise generally has a cylindrical form. The manifold shaft 60 is rotatable about a central axis thereof, most preferably by gripping and rotating a knob 61 to a portion of the shaft 60 aligned with the control slot 54 in the manifold chamber 50. Manifold shaft 60 extends between a proximal tip 63 adjacent to the tip 52 of the manifold chamber 50 to a distal tip 65 near but preferably extending slightly past the knob 61.

The three paths formed on the exterior of the manifold shaft 60 include a front path 62 selectively leading to the front port 26, a rear path 64 selectively leading to the rear port 28 and a combined path 66 which selectively leads to both the front port 26 and rear port 28 together, along a single path defined as a combined path 66 which provides for staged delivery of both fluids from the front chamber 70 followed by the rear chamber 80.

The front path 62 is preferably a short path which extends from the proximal tip 63 of the manifold shaft 60 slightly in a distal direction. Proximal tip 63 of the manifold shaft 60 preferably does not fit tightly up against the tip 52 of the manifold chamber 50 in a way which blocks flow. Rather, this proximal tip 63 preferably is held short of fully coming tightly against the tip 52 within the manifold chamber 50. This way, fluids can pass into the tip 52 and then access the front path 62 (as well as the rear path 64 and combined path 66). However, only the path 62, 64, 66 which is currently aligned with the hollow body 20 of the syringe 10 can have fluid drawn therein due to suction produced by pulling on the shaft 44 of the plunger 40, so that fluid only enters an appropriate one of the chambers 70, 80 when the plunger 40 is retracted (along arrows A and B of FIGS. 6-9).

The front path 62 is provided at a radial position on the manifold shaft 60 which is distinct from a radial position of the rear path 64 and combined path 66. In this exemplary embodiment, the front path 62 on the manifold shaft 60 is closest to the body 20 and aligned with the front port 26 when the knob 61 is in a nine o'clock position. This nine o'clock position is the position seen by a user located on a distal side of the syringe and looking in a proximal direction at the distal tip 65 of the manifold shaft 60 and portions of the manifold chamber 50 opposite the tip 52. This position for the knob 61 is shown in FIG. 2 as well as in FIGS. 8 and 9. This is typically the second orientation during a filling procedure for both chambers 70, 80.

The rear path 64 in this exemplary embodiment is "L" shaped with a sharp bend therein, between an axially extending portion and a circumferentially extending portion. With such a shape, this rear path 64 can have a length similar to a length of the piston 30, but avoid being aligned with the front port 26 when being aligned with the rear port 28 and extending to the proximal tip 63 and the tip 52. The rear path 64 is active for fluid delivery between the tip 52 and the rear chamber 80 when the knob 61 is in the three o'clock position, such as that depicted in FIGS. 1, 6 and 7.

The combined path 66 is preferably a linear path having a long length similar to a length of the piston 30. This combined path 66 is preferably linear so that it can be open to both of the front port 26 and rear port 28 when these ports 26, 28 are oriented in a common plane. This combined path 66 is active and communicating with the front port 26 and rear port 28 when the knob 61 is in a twelve o'clock position, such as that depicted in FIGS. 3, 10 and 11.

With particular reference to FIG. 4, details of an alternative syringe 110 are described, according to an alternate embodiment. In this alternative embodiment, a syringe 110 is provided which has a similar body 120 with piston 130 and plunger 140 as that associated with the first embodiment of FIGS. 1-3. Uniquely, the manifold chamber 150 includes a front valve 160 and a rear valve 170. The front valve 160 controls a fluid pathway between a tip on the manifold chamber 150 and a front chamber 180 of the body 120. A rear valve 170 regulates flow between a tip of the manifold chamber 150 and a rear chamber 190 within the body 120. The valves 160, 170 could be stopcock type valves, such as ball valves or other stopcock type valves, or could be any of a variety of different other kinds of valves. These valves could be manually actuated, such as by rotation or translation to transition between open and closed states.

As an alternative, the valves 160, 170 could be powered, such as by pneumatics, hydraulics, electronics, solenoids, springs, etc. and be integrated into a control system. Such powered valves 160, 170 would typically have a default state and then be actuatable to transition from the default state to a second state. Typically, the default state would be a closed state. When the valve is actuated, this actuation would cause the valve to move into a second state which would typically be an open state.

Valves 160, 170 would be selected for opening through some form of control interface. This control interface could be manually actuatable buttons or levers, or could be part of a control system and causing the valves to open or close responsive to some input signals. Such signals could be monitored parameters, such as within an infusion system and when a system detects a condition which warrants delivery of a fluid, an appropriate valve is opened to cause appropriate fluid filling or dispensing action. Other actuators could include voice activation or other sources of actuating inputs. Fluid pathways associated with the valves 160, 170 could be entirely separate, or at least partially shared.

With particular reference to FIG. 5, details of a manual loading guide system are disclosed. This guide system could be provided along with the embodiment of FIGS. 1-3 or along with embodiment of FIG. 4, or with other embodiments. With this guide system, rear graduation lines 6 this guide system could be provided along with the embodiment of FIGS. 1-3 or along with embodiment of FIG. 4, or with other embodiments. With this guide system, rear graduation lines 90 are provided as one set and front graduation lines 94 provided as a second set. Rear indicia 92 are provided adjacent to rear graduation lines 90. Front indicia 96 are provided adjacent to front graduation lines 94. The graduation lines 90, 94 preferably are visible lines extending circumferentially on the wall of the body 20. These graduation lines 90, 94 are preferably parallel with each other and spaced from each other axially. Spacing between graduation lines 90 preferably corresponds with increments of some volumetric quantity. As one example, each graduation line 90, 94 could be spaced apart by a distance corresponding with a volume of 1 cm$^3$ (1 mL). The indicia 92, 96 adjacent to the graduation lines 90, 94 would indicate the volume amount provided. Labeling 98 preferably is provided adjacent to the rear graduation lines 90 and the front graduation lines 94 so that one can tell whether the set of graduation lines is for a "front volume" of the syringe 10 or a "rear volume" of the syringe 10.

Importantly, the rear graduation lines 90 have a first (most proximal) graduation line with a rear indicia 92 in the form of number "zero" adjacent thereto. The first rear graduation line 90 is not located at the proximal end 22 of the body 20, as is the case with a typical syringe. Rather, this first rear graduation line 90 labeled with the rear indicia 92 of "zero" is located adjacent to the rear port 28 and spaced from the proximal end 22 of the body 20 by distance similar to a length of the piston 30. In contrast, the front graduation lines 94 start at the proximal end 22 of the body 20 and with front indicia 96 starting with "zero" adjacent to a first front graduation line 94 which is adjacent to the proximal end 22 of the body 20.

In use and operation, and with particular reference to FIGS. 6-11, as well as to FIG. 5, details of the use of operation of the syringe 10 of this invention are described, according to an exemplary embodiment. In this example, two different fluids are to be delivered sequentially to a patient. Amounts to be delivered to the patient are known quantities. To affectively deliver these fluids sequentially to the patient, the syringe 10 begins empty, as depicted in FIG. 7.

A second fluid to be delivered to the patient is first connected to the tip 52 of the manifold chamber 50, such as by connecting a vial of medicament to a stopcock which in turn is connected to the tip 52, and with the stopcock configured to provide an open pathway between the medicament and the tip 52. The plunger 40 is then retracted (along arrow D of FIG. 6). Before such retraction, the knob 61 is placed in the three o'clock position as depicted in FIG. 6. This causes the rear path 64 to be active, so that as the plunger 40 is retracted (along arrow D) fluid is caused to flow along arrow A along the rear path 64, and then curving with the rear path 64 and accessing the rear port 28 and passing through a wall of the body 20 into the hollow interior thereof. At such a location, fluid passes between the piston 30 at the rear seal 34 thereof and the plunger seal 42 of the plunger 40. This second fluid to be delivered thus fills the rear chamber 80 as the plunger 40 continues to be retracted (along arrow D and as depicted in FIG. 7). Such retraction of the plunger 40 continues until the rear chamber 80 has been filled to a desired amount as indicated on the rear volume graduation lines 90 and rear indicia 92 (FIG. 5).

Next, the knob 61 is rotated to the nine o'clock position so that the front path 62 becomes active. A source of a first medicament or other fluid to be delivered to the patient is coupled to the tip 52, such as through a stopcock or directly to the tip 52. The plunger 40 is then further retracted (along arrow D of FIG. 8) causing the second fluid to pass through the tip 52 and then along the front path 62 and into the front chamber 70 between the piston 30 and proximate end 22 of the body 20. The plunger 40 continues to be retracted along arrow D until the front chamber 70 has been filled with a desired amount of the first fluid to be dispensed. Such volumetric loading precision can be guided by observing the front graduation lines 94 and front indicia 96. The syringe 10 is now fully loaded and ready for use. The first fluid to be dispensed is in the front chamber 70 and the second fluid to be dispensed is in the rear chamber 80.

To dispense the fluids sequentially from the front chamber 70 followed by the rear chamber 80, the knob 61 is first rotated to the twelve o'clock position, as depicted in FIGS. 10 and 11. The plunger 40 is then pressed, along arrow E, causing fluid dispensing. Because the piston 30 is initially blocking the rear port 28, only the first fluid can be discharged from the front chamber 70 along the combined path 66 and out of the tip 52. The tip 52 has already been connected to the patient, such as through a needle or through a stopcock and medical tubing, or other apparatuses. Thus, the first fluid contained within the front chamber 70 is delivered into the patient.

Once all of this first fluid has been passed out of the front chamber 70, the piston 30 will be adjacent to the proximal end 22 and the rear port 28 is now open to the combined path 66 and open to the rear chamber 80. Continued pressing of the plunger 40 (along arrow E of FIG. 11), will cause flow of the second fluid from the rear chamber 80 on the combined path 66 and out of the tip 52. The second fluid is thus sequentially delivered from the rear chamber 80 after the first fluid has been delivered from the front chamber 70.

In one embodiment, the rear chamber 80 is filled with a saline flush liquid of a volumetric amount similar to that of medical tubing between the tip 52 and the patient. Thus, the second fluid within the rear chamber 80 is merely provided to cause the first fluid to not be left within the medical tubing, but be advanced entirely into the patient. Some medications are exceptionally expensive, and it is desirable to have all of the expensive medication delivered to the patient for therapeutic benefit, rather than being wasted by remaining within the medical tubing and never delivered to the patient.

In one embodiment, the procedure identified above could be preceded by filling the amount of medical tubing between the syringe 10 and the patient with a fluid such as a saline flush fluid. An amount of fluid that it takes to entirely fill this medical tubing could be measured so that a volume of the medical tubing is known. Then, on utilizing the syringe 10, an amount of the second fluid to be loaded first into the rear chamber 80, can be loaded by monitoring the rear graduation lines 90 and rear indicia 92 to match the volume of an amount of medical tubing.

In one embodiment, the rear chamber 80 can be preloaded with saline flush or other second fluid. In such an embodiment, a user would only need to load the first fluid into the front chamber 70 and discharge both fluids sequentially. In such an embodiment, as an option, only two flow paths, including the front path 62 and the combined path 66 could be provided, to simplify the manifold. As a further option, only the combined path 66 could be provided and the manifold made to not have multiple states. A burst disk could be supplied at the rear port 28 so that the rear chamber 80 remains inactive until the front chamber has been discharged of first fluid and the plunger 40 is pushed hard enough to fracture the burst disk and allow the second fluid to flow from the rear chamber 80 through the combined path 66 to the tip 52.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. For instance, while the tip 52 is shown offset laterally from the centerline of the body 20, it could have a short path to route fluid from the lateral proximal location to a centerline proximal location at the proximal end 24 to present a familiar central location for the tip 52.

When embodiments are referred to as "exemplary" or "preferred" this term is meant to indicate one example of the invention, and does not exclude other possible embodiments. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A multistage syringe, comprising in combination:
a hollow body having a proximal end opposite a distal end;
a plunger extending into the distal end of the hollow body and adapted to translate linearly within the hollow body;
a movable piston within the hollow body and between the plunger and the proximal end of the hollow body;
a front port accessing a space within the hollow body between the piston and the proximal end of the hollow body;
a rear port accessing a space within the hollow body and on a distal side of the piston when the piston is adjacent to the proximal end of the hollow body;
at least one flow path extending from an input/output tip of the syringe and selectively connectable and disconnectable to the front port and/or rear port;
wherein a front valve of the syringe is interposed between the input/output tip and the space within the hollow body between the piston and the proximal end of the hollow body; and
wherein a rear valve is interposed between the input/output tip of the syringe and the space within the hollow body on the distal side of the piston when the piston is adjacent to the proximal end of the hollow body.

2. The syringe of claim 1 wherein said hollow body is at least partially transparent and with graduation lines provided thereon and indicia visible adjacent to the graduation lines, the graduation lines beginning on a portion of the hollow body spaced from the proximal end by a distance similar to a length of the piston.

3. The syringe of claim 2 wherein said hollow body includes two sets of graduation lines and indicia, one of which sets of graduation lines and indicia beginning at a location spaced from the proximal end of the hollow body by a distance similar to a length of the piston, and the other of the set of graduation lines and indicia beginning at the proximal end of the hollow body.

4. The syringe of claim 1 wherein the front valve and the rear valve can be both open, both closed or one open and one closed.

5. The syringe of claim 1 wherein the hollow body of the syringe is at least partially transparent and with graduation lines provided on the hollow body, with indicia visible adjacent to at least one of the graduation lines.

* * * * *